United States Patent
Barry et al.

(10) Patent No.: US 8,927,862 B2
(45) Date of Patent: Jan. 6, 2015

(54) FEEDTHROUGH ASSEMBLY FOR AN IMPLANTABLE DEVICE

(71) Applicants: Patrick J. Barry, North St. Paul, MN (US); Derek John Boettger, St. Paul, MN (US)

(72) Inventors: Patrick J. Barry, North St. Paul, MN (US); Derek John Boettger, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/097,607

(22) Filed: Dec. 5, 2013

(65) Prior Publication Data

US 2014/0083762 A1    Mar. 27, 2014

Related U.S. Application Data

(63) Continuation of application No. 13/154,627, filed on Jun. 7, 2011, now Pat. No. 8,604,341.

(60) Provisional application No. 61/362,368, filed on Jul. 8, 2010.

(51) Int. Cl.
| H05K 5/06 | (2006.01) |
| H02G 3/02 | (2006.01) |
| A61N 1/05 | (2006.01) |
| A61N 1/375 | (2006.01) |

(52) U.S. Cl.
CPC .. *A61N 1/05* (2013.01); *H02G 3/02* (2013.01); *A61N 1/3754* (2013.01)
USPC .... 174/50.6; 174/650; 174/50.56; 174/50.61; 361/302; 361/306.1; 29/592.1

(58) Field of Classification Search
CPC ..... A61N 1/3754; A61N 1/3752; A61N 1/05; H01G 4/35; H01G 4/38; H01G 4/385; H01G 5/01; H01G 5/014; H01G 4/228; H01G 4/236; H05K 5/06; H05K 5/0091; H05K 5/02; H05K 5/069
USPC .............. 174/152 GM, 50.6, 650, 50.61, 520, 174/50.59, 50.56; 361/302, 306.1, 307; 607/36, 37, 5; 29/592.1, 592
See application file for complete search history.

(56) References Cited

U.S. PATENT DOCUMENTS

| 5,905,627 A | 5/1999 | Brendel et al. |
| 6,274,252 B1 | 8/2001 | Naugler et al. |

(Continued)

OTHER PUBLICATIONS

U.S. Appl. No. 13/154,627, Non Final Office Action mailed Apr. 25, 2013, 8 pgs.

(Continued)

*Primary Examiner* — Angel R Estrada
(74) *Attorney, Agent, or Firm* — Schwegman Lundberg & Woessner, P.A.

(57) ABSTRACT

A feedthrough assembly includes a metallic ferrule, an insulator mounted within the ferrule, a plurality of feedthrough wires mounted within and extending through the insulator, and a ground wire directly attached to the ferrule, wherein the ground wire does not pass through or alongside the insulator.

19 Claims, 6 Drawing Sheets

(56) References Cited

U.S. PATENT DOCUMENTS

| | | |
|---|---|---|
| 6,586,675 B1 | 7/2003 | Bealka et al. |
| 6,765,780 B2 * | 7/2004 | Brendel et al. ............... 361/302 |
| 6,768,629 B1 | 7/2004 | Allen et al. |
| 7,035,076 B1 | 4/2006 | Stevenson |
| 7,046,499 B1 | 5/2006 | Imani et al. |
| 7,187,535 B1 | 3/2007 | Iyer et al. |
| 8,160,707 B2 | 4/2012 | Iyer et al. |
| 8,604,341 B2 | 12/2013 | Barry et al. |
| 2012/0006576 A1 | 1/2012 | Barry et al. |

OTHER PUBLICATIONS

U.S. Appl. No. 13/154,627, Notice of Allowance mailed Aug. 12, 2013, 11 pgs.

U.S. Appl. No. 13/154,627, Response filed Jul. 15, 2013 to Non Final Office Action mailed Apr. 25, 2013, 7 pgs.

* cited by examiner

FEEDTHROUGH ASSEMBLY FOR AN IMPLANTABLE DEVICE

CROSS-REFERENCE TO RELATED APPLICATIONS

This application is a continuation of U.S. application Ser. No. 13/154,627, filed Jun. 7, 2011, now issued as U.S. Pat. No. 8,604,341, which claims the benefit of U.S. Provisional Application No. 61/362,368, filed on Jul. 8, 2010, under 35 U.S.C. §119(e), each of which is incorporated herein by reference in its entirety.

BACKGROUND

Implantable medical devices are used to treat many conditions. Implantable devices such as pacemakers and defibrillators include electronics mounted within a housing. The electronics are typically operatively connected to a lead which is implanted on or in the heart. The leads implanted in or about the heart can be used to reverse certain life threatening arrhythmia, or to stimulate contraction of the heart. Electrical energy is applied to the heart via electrodes on the leads to return the heart to normal rhythm.

An implantable device can include a hermetically sealed device housing electrically and mechanically connected to a header. The header is used to couple a conductor of the lead with the electronics of the implantable device. The header is electrically connected to the device housing by an electrical feedthrough assembly including feedthrough wires that extend from outside to inside the housing to connect to the electronic components within the housing.

The feedthrough assembly provides a mechanism for electrical signal transfer through the hermetically sealed housing. In some cases, a ferrule of the feedthrough assembly needs to be at electrical ground potential. In some feedthrough assemblies, such as discussed in U.S. Pat. No. 6,586,675, the ground lead connection extends through an insulator of a feedthrough assembly and is then connected to the ferrule on the exterior of the housing.

OVERVIEW

The present inventors have recognized, among other things, a need for a feedthrough assembly that can include a metallic ferrule, an insulator mounted within the ferrule, a plurality of feedthrough wires mounted within and extending through the insulator, and a ground wire that can be directly attached to the ferrule, wherein the ground wire need not pass through or alongside the insulator.

Example 1 can include subject matter that can include a feedthrough assembly, in which the feedthrough assembly can comprise: a metallic ferrule; an insulator mounted within the ferrule; a plurality of feedthrough wires mounted within and extending through the insulator; and a ground wire attached to the ferrule, wherein the ground wire does not pass through or alongside the insulator.

In Example 2, the subject matter of Example 1 can optionally comprise the ground wire being located on an interior side of the feedthrough assembly and wherein the ground wire is not exposed on an exterior side of the feedthrough assembly.

In Example 3, the subject matter of any of Examples 1-2 can optionally comprise the ground wire being centrally located with respect to the plurality of feedthrough wires.

In Example 4, the subject matter of any of Examples 1-3 can optionally comprise the ferrule including a feature to facilitate coupling of the ground wire by a braze joint.

In Example 5, the subject matter of any of Examples 1-4 can optionally comprise the ferrule having a feature to facilitate coupling of the ground wire by a weld joint.

In Example 6, the subject matter of any of Examples 1-5 can optionally comprise the ferrule including titanium.

In Example 7, the subject matter of any of Examples 1-6 can optionally comprise the insulator including an alumina ceramic.

In Example 8, the subject matter of any of Examples 1-7 can optionally comprise the ferrule including a peninsular portion located at a central location of the ferrule and wherein the ground wire is attached to the peninsular portion.

In Example 9, the subject matter of any of Examples 1-8 can optionally comprise a capacitive filter mounted around the plurality of feedthrough wires and around the ground wire.

Example 10 can comprise, or can optionally be combined with the subject matter of any of Examples 1-9 to optionally comprise, an implantable device, comprising: a housing; a header attached to the housing; a feedthrough assembly attached to the housing and being hermetically sealed. The feedthrough assembly can include: a metallic ferrule having an outer perimeter and a peninsular portion extending into a middle area of the ferrule; an insulator mounted within the ferrule; a plurality of feedthrough wires mounted within and extending through the insulator from an interior of the housing to an exterior of the housing; and a ground wire directly attached to the peninsular portion of the ferrule, wherein the ground wire does not pass through or alongside the insulator, wherein the ground wire is located on an interior side of the housing and is not exposed on an exterior side of the housing.

In Example 11, the subject matter of any of Example 1-10 can optionally comprise the ground wire being centrally located with respect to the plurality of feedthrough wires.

In Example 12, the subject matter of any of Examples 1-11 can optionally comprise the ferrule including a feature to facilitate coupling of the ground wire by a braze joint.

In Example 13, the subject matter of any of Examples 1-12 can optionally comprise the ferrule having a feature to facilitate coupling of the ground wire by a weld joint.

In Example 14, the subject matter of any of Examples 1-13 can optionally comprise the ferrule includes titanium.

In Example 15, the subject matter of any of Examples 1-14 can optionally comprise the insulator including ceramic.

In Example 16, the subject matter of any of Examples 1-15 can optionally comprise the ferrule including a peninsular portion located at the central portion of the ferrule and wherein the ground wire is attached to the peninsular portion.

In Example 17, the subject matter of any of Examples 1-16 can optionally comprise a capacitive filter mounted around the plurality of feedthrough wires and around the ground wire.

Example 18 can comprise, or can optionally be combined with the subject matter of any of Examples 1-17 to comprise a method that can include: mounting a.

insulator to a ferrule; mounting a plurality of feedthrough wires to holes with the insulator, each feedthrough wire extend through the insulator; and mounting a ground wire directly to the ferrule, wherein the ground wire does not pass through or alongside the insulator.

In Example 19, the subject matter of any of Examples 1-18 can optionally comprise the insulator being mounted to the ferrule by gold brazing.

In Example 20, the subject matter of any of Examples 1-19 can optionally comprise the feedthrough wires are mounted to the insulator by gold brazing.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
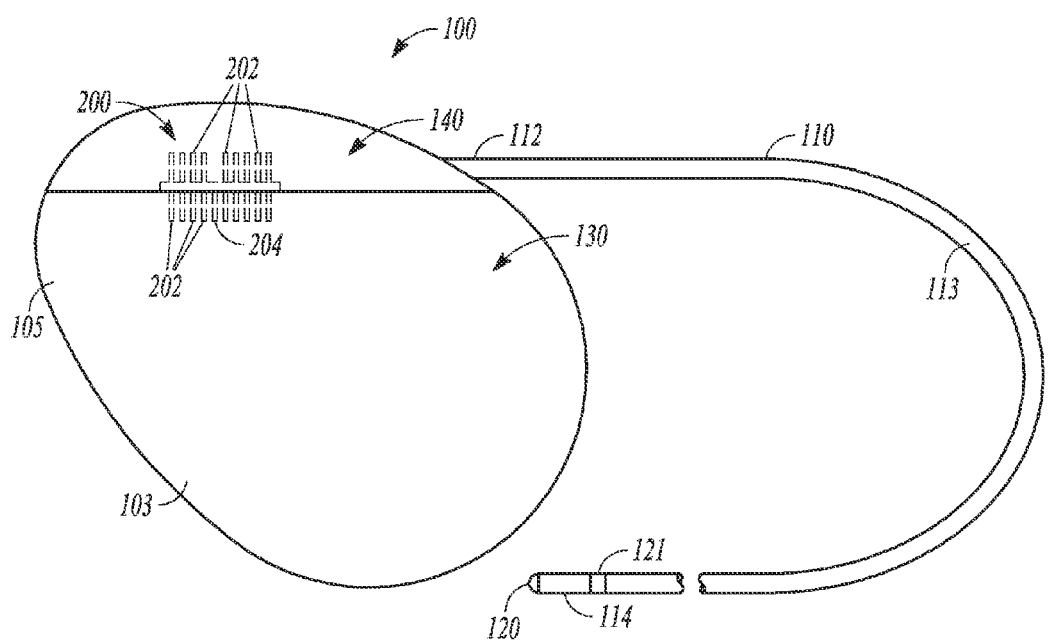
FIG. 1 shows an implantable medical device in accordance with an example.

FIG. 1 shows an implantable medical device 100, in accordance with an example. Device 1100 includes an electronics unit, such as a pulse generator 105, and at least one lead 110. The pulse generator 105 is generally implanted into a subcutaneous pocket made in the upper pectoral region. Alternatively, the pulse generator 105 is placed in a subcutaneous or submuscular pocket made in the abdomen, or in other locations. Pulse generator 105 generally includes a hermetically sealed housing 103 and a header 104. Header 104 is mechanically and electrically coupled to housing 103. Pulse generator 105 can include a power supply such as a battery, a capacitor, and other components housed in housing 103. The pulse generator 105 can also include circuitry, such as a microprocessor, to provide processing, evaluation, or to determine and deliver electrical shocks or pulses of different energy levels or timing for defibrillation, cardioversion, or pacing to a heart such as in response to cardiac arrhythmia including fibrillation, tachycardia, heart failure, and bradycardia.

Lead 110 includes a lead body 113 having a proximal end 112, where the lead is coupled to header 104 of pulse generator 105. The lead 110 extends to a distal end 114, which is coupled with a portion of a heart, when implanted. In an example, the distal end 114 of the lead 110 includes one or more electrodes 120, 121. In an example, one or more electrodes can be located medially or at other locations along the lead. At least one electrical conductor is disposed within the lead 110, such as to extend from the proximal end 112 to at least one respective electrode(s) 120, 121. The electrical conductors carry electrical current and pulses between the pulse generator 105 and the electrode(s) 120, 121, In an example, device 100 is suitable for use as or with one or more implantable electrical stimulators, such as, but not limited to, pulse generators, neuro-stimulators, skeletal stimulators, central nervous system stimulators, or stimulators for the treatment of pain. The system can also be utilized as a sensor or a receiver. The electrodes can be used, for sensing, pacing, and/or shocking, for example.

An example of a feedthrough assembly 200 is schematically shown in FIG. 1. The feedthrough assembly 200 is attached to a hole in the housing 103 and is attached so that the housing is hermetically sealed. The feedthrough assembly 200 can include a plurality of feedthrough wires 202 mounted within and extending through an insulator of the feedthrough assembly 200 from an interior 130 of the housing 103 to an exterior 140 of the housing 103. The feedthrough assembly 200 further includes a ground wire 204 directly attached to a ferrule of the feedthrough assembly 200. As will be discussed in further detail below, the ground wire 204 does not pass through or alongside the insulator of the feedthrough assembly 200. Instead, in an example, the ground wire 204 can be located and attached to electronics on the interior side 130 of the housing 103 and is not exposed on the exterior side 140 of the housing 103.

Figure 2:
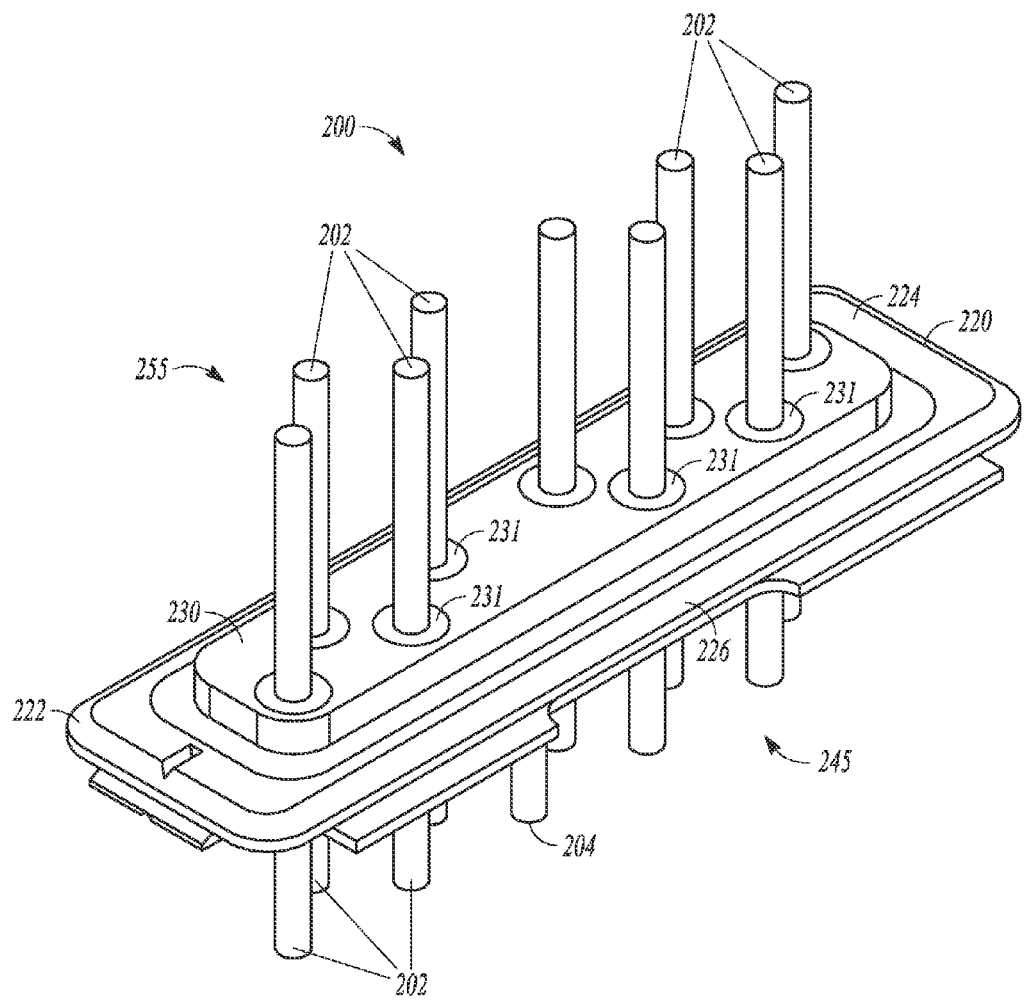
FIG. 2 shows a top perspective view of a feedthrough assembly for an implantable medical device, in accordance with an example.
Figure 3:
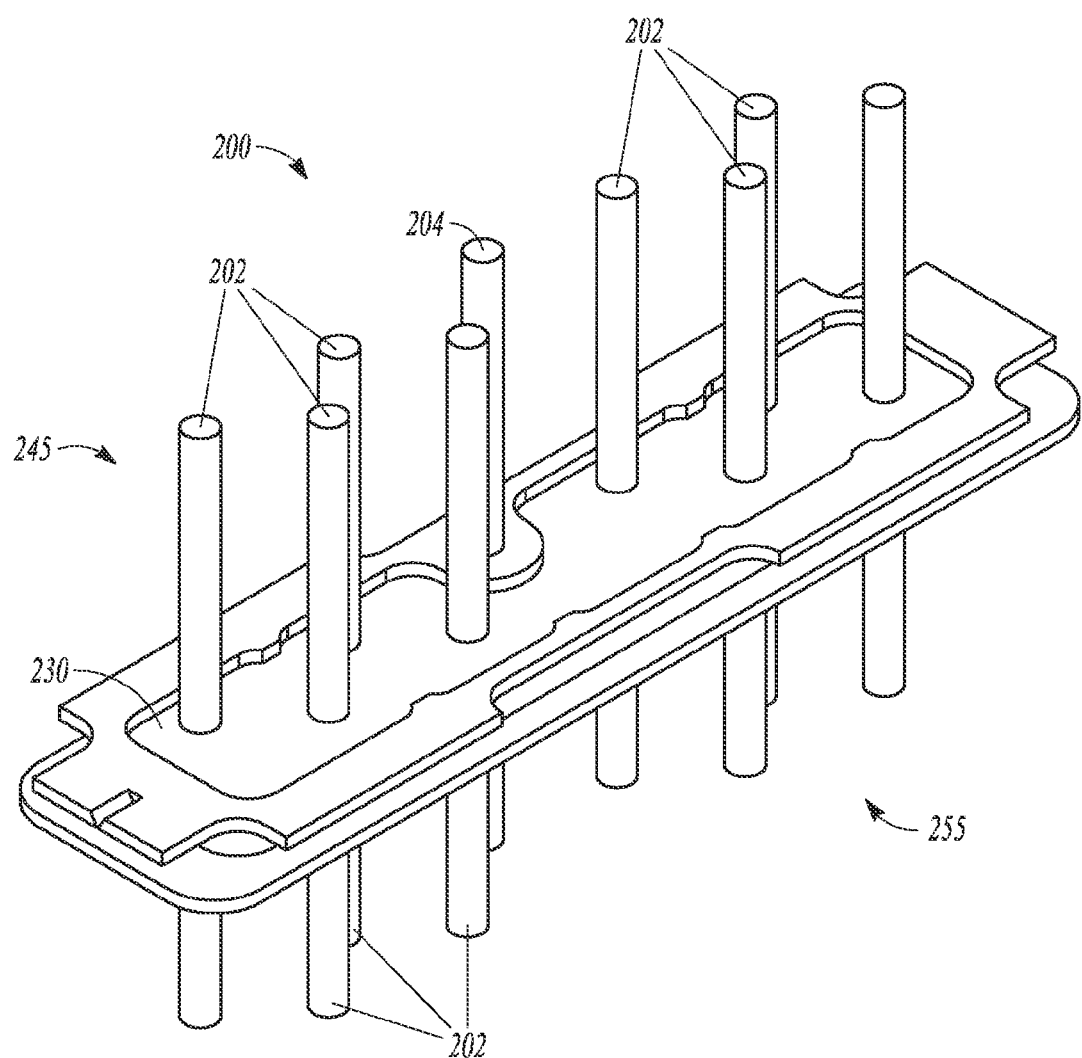
FIG. 3 shows a bottom perspective view of the feedthrough assembly of FIG. 2.

FIG. 2 shows a top perspective view of the feedthrough assembly 200, and FIG. 3 shows a bottom perspective view of the feedthrough assembly 200, in accordance with an example. The feedthrough assembly 200 includes an elongate metallic ferrule 220 having a first end 222 a second end 224 and a central portion 226 between the first end 222 and the second end 224. In an example, the ferrule 220 is mounted to the housing of the implantable device by fitting the ferrule into a hole in the housing and laser welding the ferrule 220 at an outer perimeter of the ferrule 220. In certain examples, the ferrule 220 is formed of titanium.

An insulator 230 is mounted within the ferrule 220. In certain examples, the insulator 230 includes a ceramic material, such as an alumina ceramic. The insulator 230 can be mounted to the ferrule 220 using gold brazing, for example. The insulator 230 includes a plurality of holes 231 extending through the insulator 230. The plurality of feedthrough wires 202 are mounted within and extend through the respective holes 231 of the insulator 230 from an interior side 245 of the feedthrough assembly 200 to an exterior side 255 of the feedthrough assembly 220. The feedthrough wires 202 are hermetically connected to the insulator 230 at the holes 231 using a gold-brazed joint, for example.

The ground wire 204 is directly attached to the central portion 226 of the ferrule 220. In certain examples, the ground wire 204 is centrally located along feedthrough assembly 200 with respect to the plurality of feedthrough wires 202. The ground wire 204 does not pass through or alongside the insulator 230. The ground wire 230 is located on the interior side 245 and is not exposed on the exterior side 255 and thus does not require hermetic connection. By not allowing the ground wire 204 to pass through or alongside the insulator 230, the present feedthrough assembly 200 has one less potential leak path that could compromise the hermetic seal of the feedthrough assembly 200. The fewer number of holes or other leak paths through the insulator 230 provides for a more robust hermetic seal. Thus, this present structure reduces the number of hermetic connections required for a feedthrough assembly since making a ground connection on the exterior side 255 of the feedthrough assembly 200 would require that a hermetic seal be established around the ground lead as it passes through or alongside the insulator. Accordingly, the present structure eliminates such a hermetic seal requirement for the ground connection itself.

Figure 4:
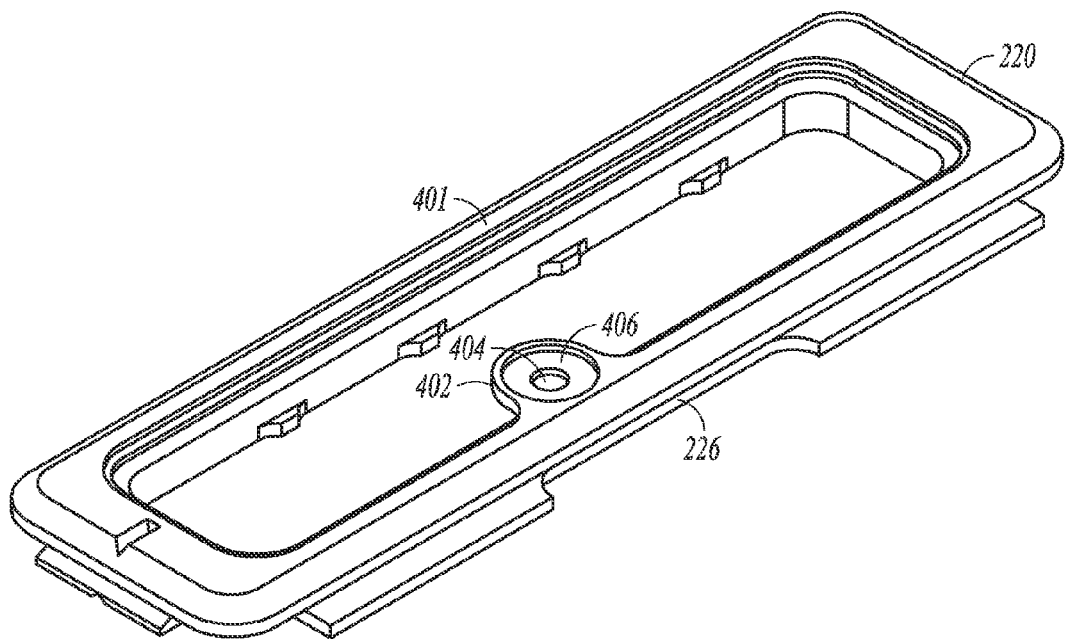
FIG. 4 shows a top perspective view of a ferrule for a feedthrough assembly, in accordance with an example.
Figure 5:
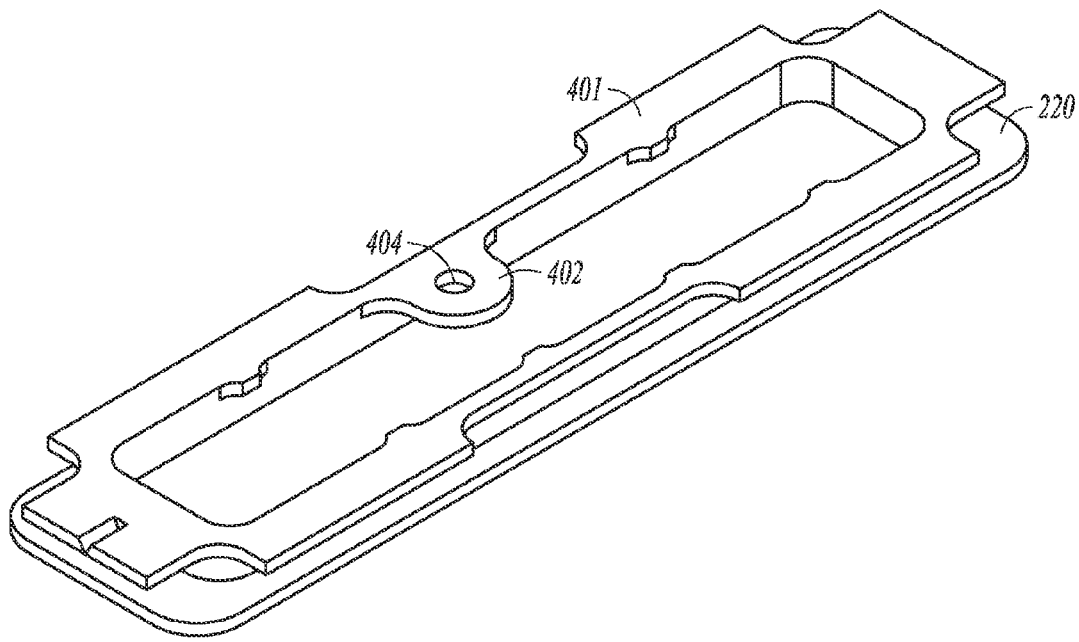
FIG. 5 shows a bottom perspective view of the ferrule of FIG. 4.

FIG. 4 shows a top perspective view of the ferrule 220, and FIG. 5 shows a bottom perspective view of the ferrule 220, in accordance with an example. The ferrule 220 includes an outer perimeter portion 401 and a peninsular portion 402 located at the central portion 226 of the ferrule 220 and extending toward the middle area inside of the ferrule 220. Referring also to FIG. 3, the ground wire 204 is attached directly to the peninsular portion 402 of the ferrule 220. The peninsular portion 402 allows the ground wire 204 to be positioned among the grouping of feedthrough wires 202.

In an example, the peninsular portion 402 includes a central hole 404 that the ground wire 204 fits within. In certain examples, to attach the ground wire 204 to the ferrule 220, a gold donut-shaped member is placed within a relief section 406 on the top side of the peninsular portion 402. The ground wire 204 is inserted within the hole 404 and the ground wire 204 is attached to the ferrule 220 using a gold-brazed joint. The present system allows making all braze connections in the feedthrough assembly 200 in one brazing temperature cycle.

In certain examples, the ground wire 204 can be welded to the peninsular portion 402. In that case, the welding can be done either before or after the assembly and brazing processes to enable a process that is most efficient.

Figure 6:
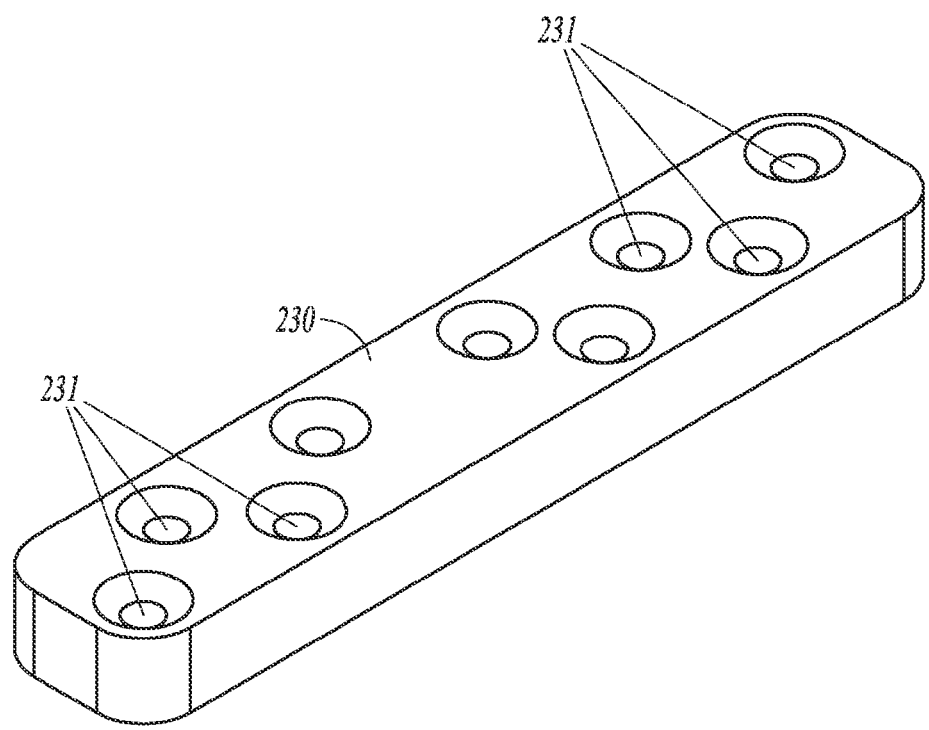
FIG. 6 shows a top perspective view of an insulator for a feedthrough assembly, in accordance with an example.
Figure 7:
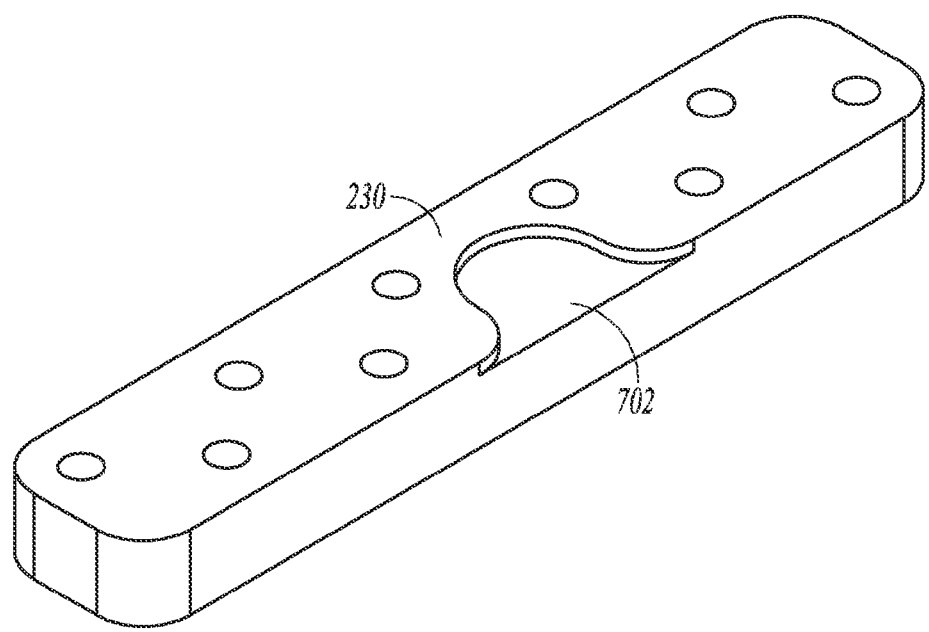
FIG. 7 shows a bottom perspective view of the insulator of FIG. 6.

FIG. 6 shows a top perspective view of the insulator 230, and FIG. 7 shows a bottom perspective view of the insulator 230. Insulator 230 includes an elongate body shaped to fit within the ferrule, as discussed above. The plurality of holes 231 include an upper beveled relief section to provide space for the gold material when the feedthrough wires are hermetically connected to the insulator 230 by brazing, for example. In certain examples a notch 702 is formed on the bottom surface of the insulator 230 to provide space for the peninsular portion 402 of the ferrule 220 discussed above. (See FIG. 5). Certain examples omit the notch 702.

Figure 8:
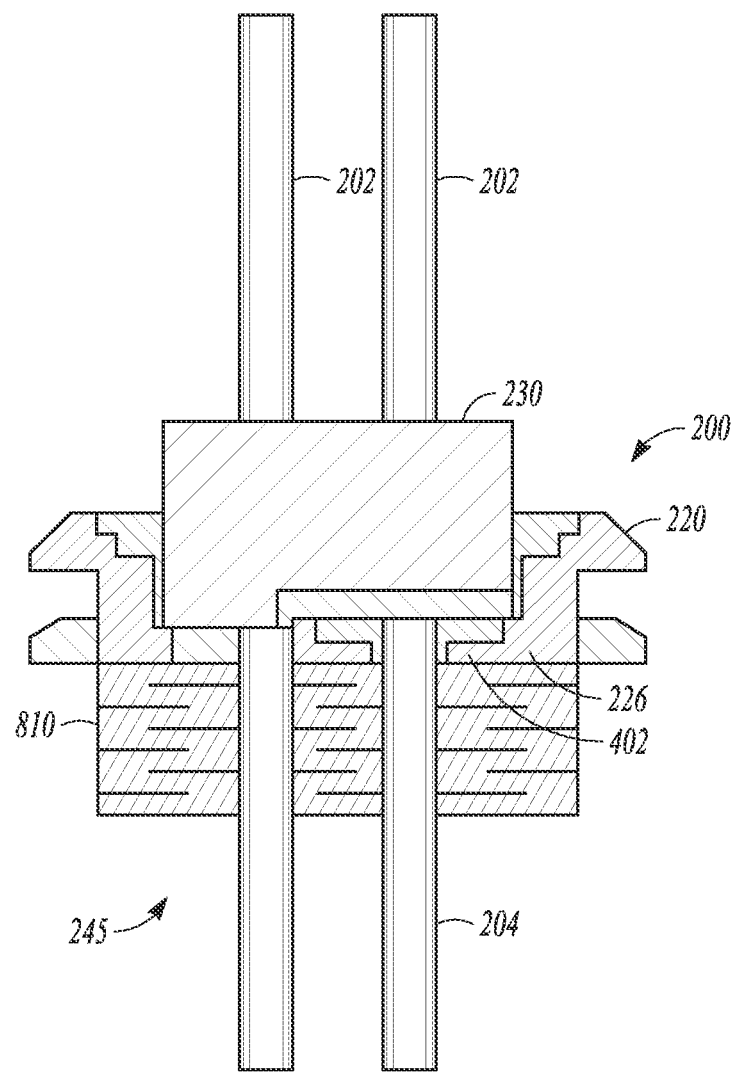
FIG. 8 shows a cross-section of a filtered feedthrough assembly, in accordance with an example.

FIG. 8 shows a cross-section of the filtered feedthrough assembly 200, in accordance with an example. In this example, a capacitive filter 810 is attached to the interior side 245 of the feedthrough assembly 200 to provide a filtered feedthrough assembly. The capacitive filter 810 is mounted around the plurality of feedthrough wires 202 and around the ground wire 204. Adding the capacitive filter 810 to the feedthrough assembly 200 provides for a hermetically sealed, filtered electrical feedthrough assembly with an internal ground connection, suitable for direct filtering of EMI and MRI signals for applications such as implantable medical devices.

In the present example, the location of the ground wire 204 at the central portion 226 of the ferrule 220 on inwardly extending peninsular portion 402 also provides a good ground connection for EMI and MRI filtering purposes since the ground wire 204 is centrally located relative to the plurality of feedthrough wires 202. A better filtering efficiency is accomplished by using the centrally located ground connection to the feedthrough assembly 200 in order to assure the lowest connection resistance, often termed effective series resistance or ESR. This feedthrough assembly design features an integrated ground connection for internal attachment to electronic devices and facilitates the required grounding of a filter capacitor device without necessitating a hermetic seal for the ground connection. Certain examples omit the capacitive filter 810 and provide an unfiltered feedthrough assembly. Other examples include other types of active filtering.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A feedthrough assembly comprising:
    a metallic ferrule including an outer perimeter and an inner perimeter, wherein a mounting section of the inner perimeter extends inward;
    an insulator mounted within the ferrule;
    a plurality of feedthrough wires mounted within and extending through the insulator; and
    a ground wire attached to the ferrule, wherein the ground wire does not pass through or alongside the insulator, and wherein the ground wire is attached to the ferrule at the mounting section such that the ground wire is positioned among the plurality of feedthrough wires.

2. The feedthrough assembly of claim 1, wherein the ground wire is located on an interior side of the feedthrough assembly and wherein the ground wire is not exposed on an exterior side of the feedthrough assembly.

3. The feedthrough assembly of claim 1, wherein the ground wire is centrally located with respect to the plurality of feedthrough wires.

4. The feedthrough assembly of claim 1, wherein ferrule includes a feature to facilitate coupling of the ground wire by a braze joint.

5. The feedthrough assembly of claim 1, wherein the ferrule has a feature to facilitate coupling of the ground wire by a weld joint.

6. The feedthrough assembly of claim 1, wherein the ferrule includes titanium.

7. The feedthrough assembly of claim 1, wherein the insulator includes an alumina ceramic.

8. The feedthrough assembly of claim 1, wherein the mounting section is located at a central location of the ferrule.

9. The feedthrough assembly of claim 1, further including a capacitive filter mounted around the plurality of feedthrough wires and around the ground wire.

10. An implantable device comprising:
a housing;
a header attached to the housing;
a feedthrough assembly attached to the housing and being hermetically sealed, the feedthrough assembly including:
a metallic ferrule including an outer perimeter and an inner perimeter, wherein a mounting section of the inner perimeter extending into a middle area of the ferrule;
an insulator mounted within the ferrule;
a plurality of feedthrough wires mounted within and extending through the insulator from an interior of the housing to an exterior of the housing; and
a ground wire directly attached to the mounting section of the ferrule, wherein the ground wire does not pass through or alongside the insulator, wherein the ground wire is located on an interior side of the housing and is not exposed on an exterior side of the housing.

11. The feedthrough assembly of claim 10, wherein the ground wire is centrally located with respect to the plurality of feedthrough wires.

12. The feedthrough assembly of claim 10, wherein ferrule includes a feature to facilitate coupling of the ground wire by a braze joint.

13. The feedthrough assembly of claim 10, wherein the ferrule has a feature to facilitate coupling of the ground wire by a weld joint.

14. The feed through assembly of claim 10, wherein the ferrule includes titanium.

15. The feedthrough assembly of claim 10, wherein the insulator includes ceramic.

16. The feedthrough assembly of claim 10, further including a capacitive filter mounted around the plurality of feedthrough wires and around the ground wire.

17. A method comprising:
mounting a insulator to a ferrule;
mounting a plurality of feedthrough wires to holes with the insulator, each feedthrough wire extend through the insulator; and
mounting a ground wire directly to the ferrule, wherein the ferrule includes a mounting section on an inner perimeter of the ferrule extending into a middle area of the ferrule, and wherein the ground wire is attached to the mounting section, and wherein the ground wire does not pass through or alongside the insulator.

18. The method of claim 17, wherein the insulator is mounted to the ferrule by gold brazing.

19. The method of claim 17, wherein the feedthrough wires are mounted to the insulator by gold brazing.

* * * * *